United States Patent [19]

Anderson, Jr. et al.

[11] Patent Number: 4,813,925
[45] Date of Patent: Mar. 21, 1989

[54] SPIRAL URETERAL STENT

[75] Inventors: Donald L. Anderson, Jr., Racine; James T. Maerzke, Kenosha, both of Wis.

[73] Assignee: Medical Engineering Corporation, Racine, Wis.

[21] Appl. No.: 40,959

[22] Filed: Apr. 21, 1987

[51] Int. Cl.⁴ ............................................. A61M 27/00
[52] U.S. Cl. ........................................ 604/8; 604/54; 604/93; 604/281
[58] Field of Search ............... 604/8, 21, 93, 164–170, 604/264, 280–282

[56] References Cited

U.S. PATENT DOCUMENTS

| | | | |
|---|---|---|---|
| 2,212,334 | 8/1940 | Wallerich | 604/280 |
| 3,938,529 | 2/1976 | Gibbons | 604/8 |
| 4,531,933 | 7/1985 | Norton et al. | 604/281 |
| 4,610,657 | 9/1986 | Denson | 604/8 |
| 4,643,716 | 2/1987 | Drach | 604/281 |
| 4,671,795 | 6/1987 | Mulchin | 604/281 |
| 4,681,570 | 7/1987 | Dalton | 604/281 |

FOREIGN PATENT DOCUMENTS 1250058 9/1967 Fed. Rep. of Germany ........ 604/93

Primary Examiner—Dalton L. Truluck
Attorney, Agent, or Firm—Stuart E. Krieger

[57] ABSTRACT

A spiral ureteral stent is positioned in the ureter to aid in infusion of the renal pelvis and to maintain fluid drainage between the renal pelvis and the bladder. The stent includes a helical coiled section having retaining means at the distal and proximal ends for reception in the bladder and the renal pelvis. The retaining means enable the stent to resist movement in the ureter. A lumen extends the entire length of the stent to form a fluid passageway for infusion of fluid from an external source into the renal pelvis. The stent is flexible and may be straightened by means of a wire stylet inserted in the lumen, to faciliate placement of the stent in the ureter. The retention means and helical coiled section reform upon withdrawal of the stylet from the lumen. As the helical coiled section reforms to its coil shape, it bears agains the walls of the ureter to reduce any restriction and to reinforce the walls of the ureter. The stent thus helps to redefine the ureteral passage from the renal pelvis to the bladder through which fluids and other matter may readily flow.

20 Claims, 3 Drawing Sheets

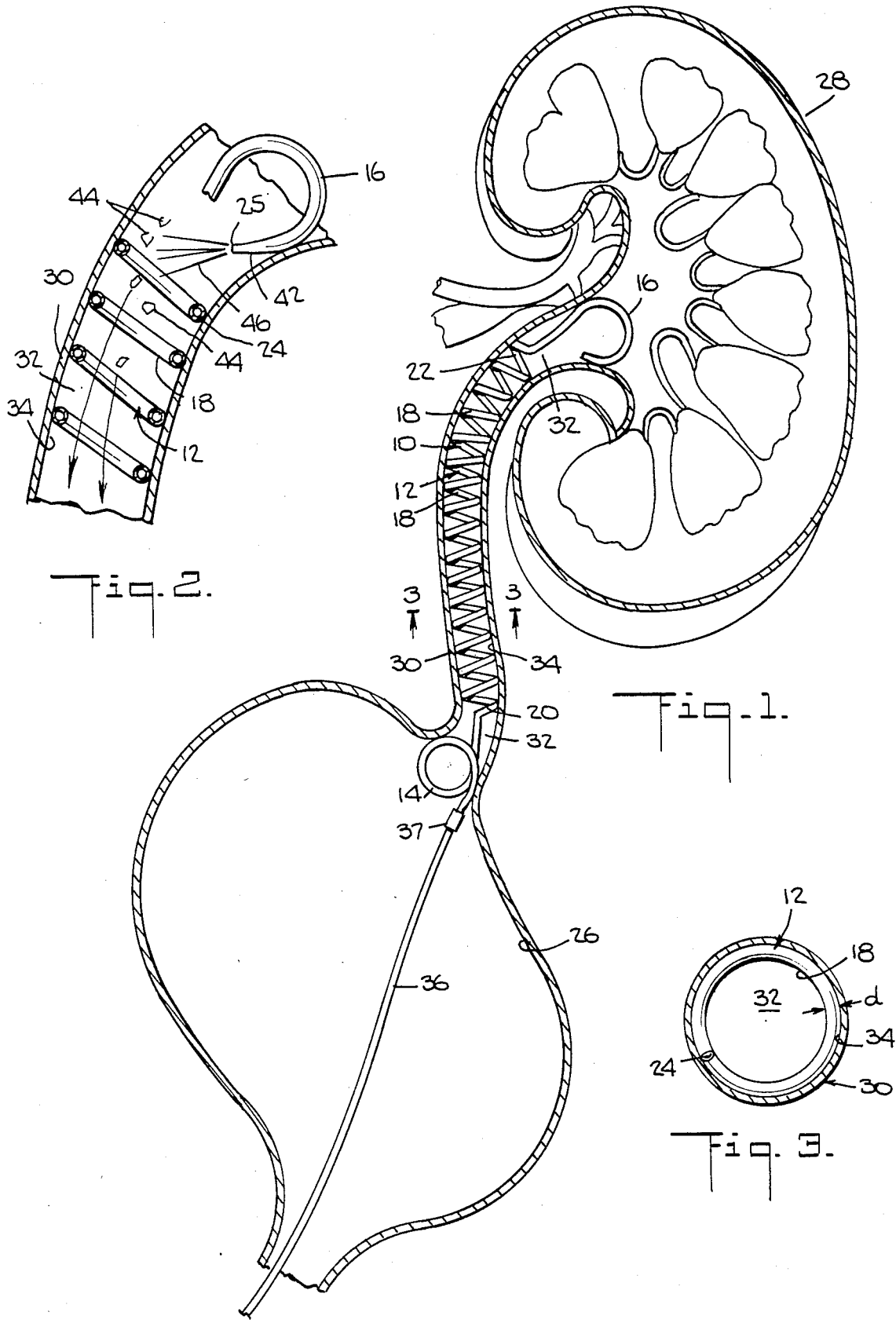

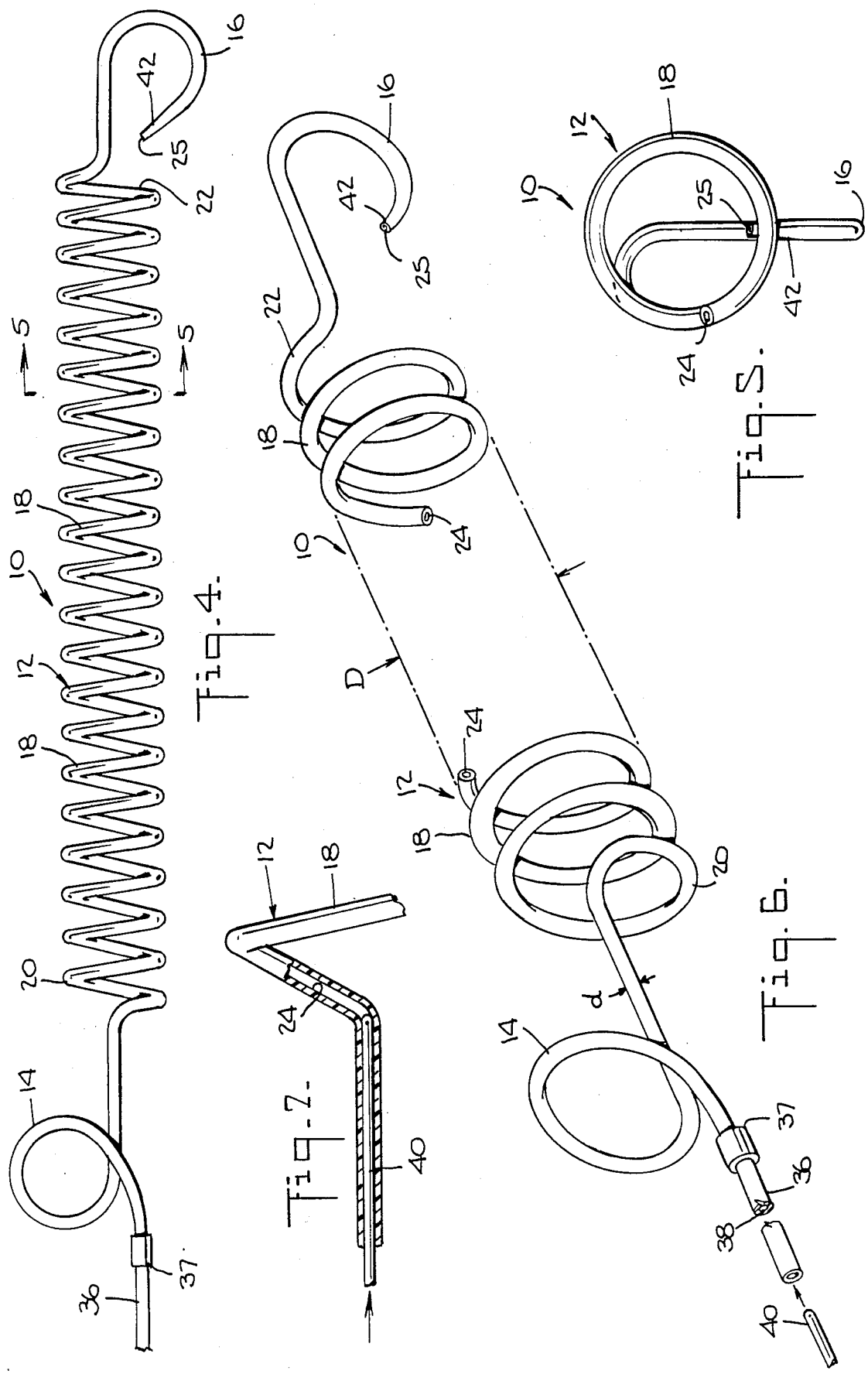

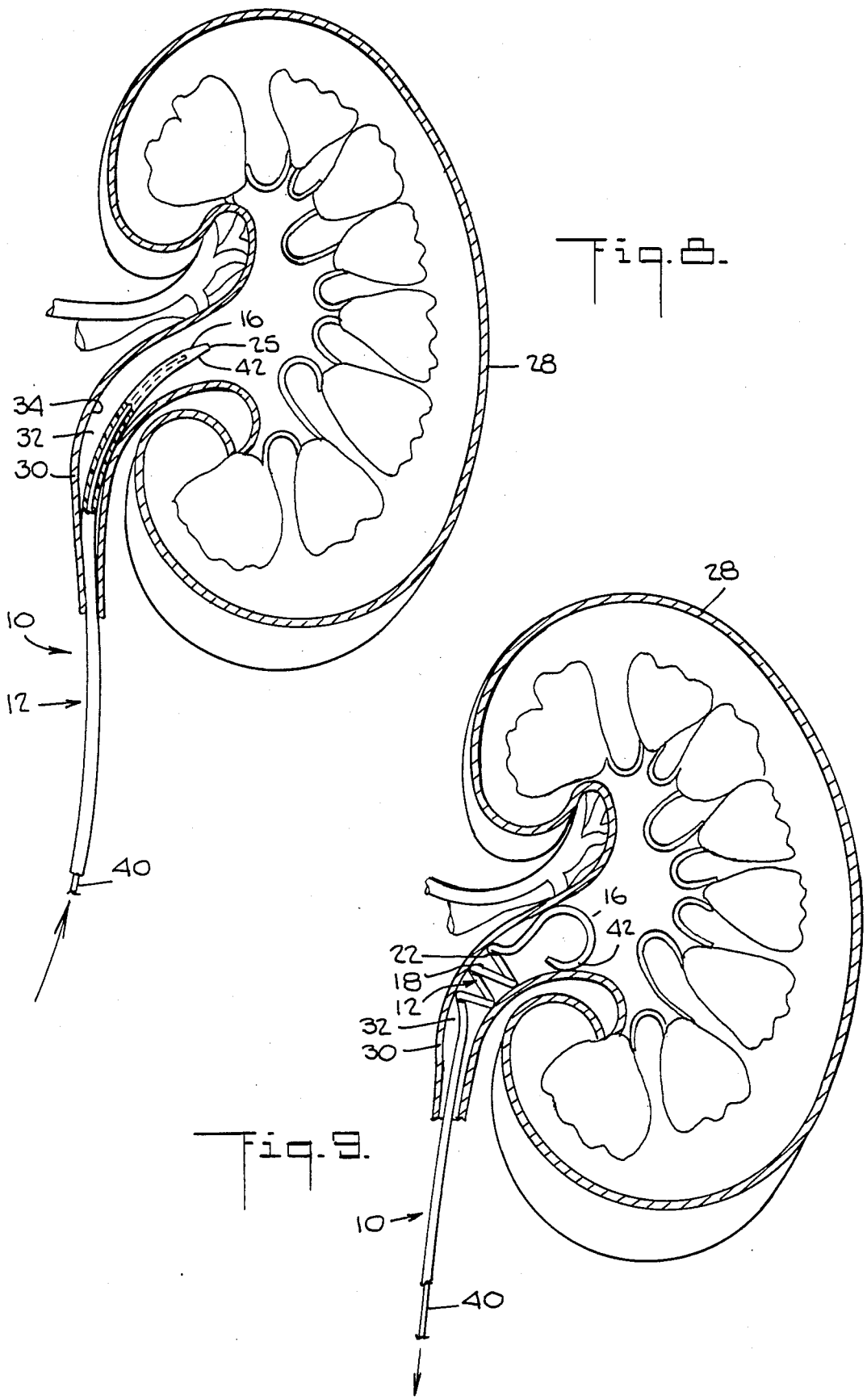

SPIRAL URETERAL STENT

BACKGROUND OF THE INVENTION

This invention relates to ureteral stents, and more particularly to a novel ureteral stent that resists migration when positioned in a patient, and facilitates infusion and drainage of the renal pelvic cavity.

Ureteral stents are often used to maintain fluid drainage from the renal pelvis to the bladder when the ureter is obstructed or otherwise impaired. The ureteral stent is usually provided with a drainage means, such as a lumen for directing fluid from the renal pelvis to the bladder.

For example, one known stent has a lumen extending its entire length with open proximal and distal ends. Alternatively, as shown in U.S. Pat. No. 4,531,933, openings may be provided along the stent for communication with the lumen to aid in drainage. Another known stent includes longitudinal grooves on the outer walls that function as fluid drainage channels. However, if the openings or channels of the lumen become encrusted with residues from the fluid being drained then the drainage capability of the stent is greatly impaired.

Occasionally a patient's medical treatment may require infusion of fluid from an external source into the renal pelvis to flush stone fragments and other debris that result, for example, from extra-corporeal shockwave stone-bursting procedures. Most stents that are used for fluid drainage purposes do not adequately flush stone bursting debris because the openings in such stents are likely to become clogged by the material that is flushed from the renal pelvis during such drainage.

It is thus desirable to provide a stent which can be used for infusion purposes and which also promotes ureteral drainage of non-liquid debris as well as fluid.

Some known ureteral stents are positioned in a patient on a temporary basis until a surgical procedure is performed, while other known stents can be left indwelling on a long-term basis as a permanent means of diverting and draining fluid.

In recent years there has been an emphasis directed toward providing a stent with stabilizing means to prevent upward or downward migration from a predetermined position in a patient. Such stabilizing means can include flexible, laterally extending barbs as shown in U.S. Pat. No. 3,938,529, opposed hook-shaped elements on the proximal and distal ends of the stent for retention, as shown in U.S. Pat. No. 4,307,723, or retention coils formed on the proximal and distal ends of the stent, as shown in U.S. Pat. No. 4,531,933.

While the known stabilizing devices enable the stent to resist migration, they do not enhance the infusion and/or drainage capability of the renal pelvis.

It is thus further desirable to provide a ureteral stent which resists migration in a patient and also enhances the infusion and drainage of the renal pelvis.

OBJECTS AND SUMMARY OF THE INVENTION

Among the several objects of the invention may be noted the provision of a novel ureteral stent, a novel ureteral stent which resists migration and enhances ureteral drainage, a novel ureteral stent for infusing fluid from an external source into the ureteral pelvis and expanding the walls of the ureter to compensate for any fluid flow restrictions therein, and a novel method of infusing fluid into the renal cavity and draining fluid through the ureter.

Other objects and features of the invention will be in part apparent and in part pointed out hereinafter.

In accordance with the present invention, the ureteral stent includes a relatively flexible, helically shaped, coiled section, selectively deformable into an approximate straight-line configuration. The coiled section, which is positioned in the ureter, has a diameter substantially equivalent to that of a normal ureter.

A first curved retention means on the distal end of the coiled section is adapted to be received in the bladder. A second curved retention means on the proximal end of the coiled section is adapted to be received in the renal pelvis. The retention means stabilize the position of the coiled section in the ureter.

A lumen extends through the entire length of the stent to provide a fluid passage therethrough. The lumen also accommodates a wire stylet that straightens the coiled section and the first and second retention means, enabling the stent to be easily inserted through the ureter. The wire stylet is removed after the stent has been properly positioned in a patient. Withdrawal of the wire stylet from the lumen enables the curved retention means at the proximal and distal ends to reassume their curved forms, and the section intermediate the proximal and distal ends, to reassume its coiled configuration.

When the stent is in its functional position within the ureter, with the stylet removed, the coiled section reinforces the internal walls of the ureter and expands any collapsed wall portions of the ureter to approximately normal size. Thus the stent compensates for any restrictions in the ureter due to collapse of the ureter wall.

The stent may also be joined at the distal end with an infusion tube. Fluid can then be infused from an external source through the infusion tube and through the lumen to the renal pelvis, to flush liquid and non-liquid materials from the pelvis through the ureter.

Fluid flow between the renal pelvis and bladder through the ureter is thus enhanced and is unimpeded by the presence of the stent. In addition, the flushing of debris or fragments that result from shock wave stone bursting procedures is greatly facilitated.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a ureteral stent incorporating one embodiment of the invention, positioned between the renal pelvis and the bladder;

FIG. 2 is an enlarged fragmentary sectional view of the distal end thereof;

FIG. 3 is an enlarged sectional view taken on the line 3—3 of FIG. 1;

FIG. 4 is a front elevational view thereof;

FIG. 5 is an enlarged sectional view taken on the line 5—5 of FIG. 4;

FIG. 6 is an enlarged perspective view thereof, prior to insertion of a stylet;

FIG. 7 is an enlarged fragmentary view thereof, partly shown in section, with the stylet partially inserted therein;

FIG. 8 is a fragmentary schematic view thereof, positioned in the ureter, with a fully inserted stylet, and the distal end thereof positioned at the renal pelvis; and, FIG. 9 is a view similar to FIG. 8 with the stylet being withdrawn from the stent.

Corresponding reference characters indicate corresponding parts throughout the several views of the drawings.

DETAILED DESCRIPTION OF THE INVENTION

A ureteral stent incorporating one embodiment of the invention is generally indicated by the reference number 10 in FIG. 1.

The ureteral stent 10 includes a coiled section 12 with a loop-shaped distal end portion 14, and a curl-shaped proximal end portion 16. The coiled section 12 comprises a plurality of coils 18 in a substantially helical configuration.

The loop-shaped distal end portion 14, which extends from a terminal coil 20 of the coiled section 12 lies in the axial plane of the helix of coils 18, as best seen in FIG. 4. The curl-shaped proximal end portion 16, which extends from an opposite terminal coil 22 of the coiled section 12, also lies in an axial plane of the helix of coils 18, as best seen in FIGS. 4 and 5. The loop-shaped distal end portion 14 and the curl-shaped proximal end portion 16 may lie within the same plane, or may be offset if desired.

Preferably the stent 10 is formed of a soft flexible biocompatible material, such as silicone. The stent 10 is thus slightly extensible or contractible in length due to the flexibility of the coiled section 12.

A lumen 24 extends through the entire length of the stent 10 with an opening (not shown) at the distal end 14 and a corresponding opening 25 (FIG. 6) at the proximal end 16. The stent 10 has a predetermined nominal extent such that when the coiled section 12 is in the ureter 30 of a patient the distal end 14 is received in the bladder 26 and the proximal end 16 is received in the renal pelvis 28.

With the stent 10 positioned as shown in FIG. 1, the coiled section 12 occupies substantially the entire length of the ureter 30, which connects the bladder 26 and the renal pelvis 28.

The coil diameter D of the coiled section 12 (FIG. 6) has a predetermined magnitude that is substantially the same or slightly larger than the internal passage 32 of the ureter 30 in its normal unimpaired state. Thus the coils 18 bear against the inside wall 34 of the ureter 30 to maintain the ureter passage 32 at a diameter equivalent to that of a normal unimpaired ureter. The stent 10 thus functions as a flexible skeletal structure for supporting the ureter wall 34.

Referring to FIGS. 3 and 6, the coil diameter D of the coiled section 12 is substantially larger than the outside diameter d of the stent 10 when the stent 10 is positioned in the ureter 30. Thus, the stent 10 helps define a passageway within and without the coils 18 along the entire length of the ureter 30.

As best seen in FIG. 1, the outer diameter of the loop-shaped distal end 14 is greater than the diameter of the ureter passage 32 where the ureter 30 joins the bladder 26. The outer curvature of the curl-shaped proximal end 16 is of a greater magnitude than the inside passage 32 of the ureter 30 where the ureter 30 joins the renal pelvis 28. The curl-shaped proximal end 16 extends more than 180° but less than 360° as best seen in FIG. 4.

The distal end 14 and the proximal end 16 prevent upward and downward migration of the stent 10 once it has been positioned in the ureter 30. The distal and proximal ends 14 and 16 thus function as retention means for retaining the stent 10 in the ureter.

A tube or infusion line 36 is engageable with the distal end 14 of the stent 10 by means of a coupling member 37 (FIG. 6) or other suitable known junction arrangement. In some instances it may be desirable that the infusion line 36 be detachable from the stent 10. The infusion line 36 includes a lumen 38 that aligns with the lumen 24 of the stent 10.

The expansible and contractable character of the stent 10 enables it to be adapted to fit a given size range of ureters. Nevertheless, differences in the length and diameter of the ureter passageway of different individuals may warrant a sizing of stents 10 according to known parameters of the ureter, the bladder and the renal cavity.

The precise dimensions of the stent 10 may vary based on the dimensional characteristics of a particular patient. Nevertheless, to exemplify the magnitudes being dealt with, the outside diameter d of the stent can be in the range of 0.131–0.079 inches, and the inside diameter of the lumen 24 can be 0.010 inches. The diameter of the coils 18 can be 0.112 inches, the nominal length of the coiled section can be 20 cm, and the overall length of the stent 10 can be 34 cm.

Once a physician has selected a stent 10 for use in a patient, after considering the normal size of the ureter passage and the length of the ureter between the renal pelvis 28 and the bladder 26, a wire stylet 40, which can be formed of stainless steel, is inserted into the distal end 14 of the stent 10, preferably through the infusion line 36 and into the lumen 24.

The stent 10 is then drawn over the stylet 40 in the manner shown in FIG. 7 to straighten the loop-shaped distal end 14, the coiled section 12 and the curled proximal end 16. Referring to FIG. 8, the stylet 40 is inserted up to, but not beyond the proximal end opening 25 of the stent 10, and can be immobilized in the stent 10, by any suitable known locking means (not shown) provided on the infusion line 36. If desired, the end opening 25 can be reduced to form a stop surface for the stylet 40 that prevents projection of the stylet 40 from the proximal end portion 16.

The infusion line 36 and the stent 10 are inserted in a patient, in a manner similar to the insertion of a conventional ureteral catheter. A tip portion 42 of the proximal end 16 can be gradually tapered to faciliate insertion of the stent 10 and also provide the reduction of the end opening 25.

Confirmation that the renal pelvis 28 has been entered by the stent 10 can be obtained by x-ray. If desired radio-opaque measurement markings or other suitable radio-opaque indicia (not shown) can be incorporated on the periphery of the stent 10 and rendered visible during x-ray examination to aid in confirming the position of the stent 10.

After the stent 10 has been inserted a predetermined distance into the renal pelvis, such as shown in FIG. 8, the wire stylet 40 is withdrawn, enabling the curl-shaped proximal end 16 to assume its normal position as shown in FIG. 9. Continued withdrawal of the stylet 40 enables the coiled section 12 to assume its coiled, helical configuration throughout the length of the ureter 30.

As the coiled section 12 reforms to its coil shape, the coils 18 bear against the walls 34 of the ureter 30 to expand any restriction and restore the ureter passage 32 to its more natural dimension as shown in FIG. 4. The coiled section 12 thus serves to reinforce a collapsed or otherwise impaired ureter 30.

When the wire stylet 40 is removed from the looped distal end 14 of the stent 10, the loop 14 is reformed in the bladder 26. The stent 10 is thus securely positioned within the ureter 30, as migration of the stent is prevented by the looped distal end 14 and the curled proximal end 16.

Since the coiled section 12 of the stent 10 acts as an expansion device to enlarge collapsed or otherwise impaired portions of the ureter 30 it facilitates fluid flow between the renal pelvis 28 and the bladder 26. It should also be noted that the stent 10 will not interfere with natural peristaltic action because of the soft pliable spring-like construction.

Alternatively, the ureteral stent 10 may be placed in the ureter 30 during open surgery. Under either installation arrangement, the ureteral stent 10 allows infusion of fluid from an external source through the infusion tube 36 to the renal pelvic area 28 through the opening 25 at the proximal end 16 of the stent 10.

The stent 10 of the present invention is particularly suitable for use during and after extra corporeal shock wave stone bursting procedures that are used to flush stone fragments 44 (FIG. 2) from the renal pelvis 28.

As shown in FIG. 2, infusion liquid 46 from an external source (not shown) is directed through the infusion line 36 and the stent 10 for efflux from the opening 25 of the proximal end 16. The infusion liquid 46 flushes the stone fragments 44 through the ureter 30.

Since the mid-section 12 reinforces and expands any collapsed areas in the ureter 30, passage of stone fragments 44 and other non-fluid debris through the ureter 30 is substantially enhanced.

If desired, the infusion tube 36 can be removed and the stent 10 left indwelling to facilitate fluid drainage from the renal cavity 28 to the bladder 26.

Some advantages of the present invention evident from the foregoing description include a ureteral stent that can be securely positioned within a ureter and which stent will permit infusion of fluid from an external source to the renal pelvis. A further advantage of the stent is its ability to expand and reinforce any collapsed areas in the ureter to enhance drainage, without inhibiting natural peristaltic action. The stent 10 thus functions as a flexible skeletal support structure.

In view of the above, it will be seen that the several objects of the present invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. A stent for placement in a ureter comprising,
   (a) a relatively flexible, helically-shaped coiled section selectively deformable into an approximately straight configuration, said coiled section having a diameter substantially the same of that of a normal unimpaired ureter to support said ureter,
   (b) a first curved retention means for holding said stent in a fixed position in the ureter formed at a distal end of said coiled section and adapted to be received in the bladder,
   (c) a second curved retention means for holding said stent in a fixed position in a ureter, formed at a proximal end of said coiled section and adapted to be received in the renal pelvis,
   (d) a lumen extending through the entire length of said stent to provide a fluid passage and to permit the use of a straightening member to straighten the coiled section and the first and second retention means such that the stent can be inserted to a predetermined position within the ureter, said straightening member being removable from the stent when the stent is in said predetermined position, to permit the coiled section to return to the helical configuration to support the wall of said ureter, and to permit said first and second retention means to reform and prevent said stent from migrating from said predetermined position.

2. The stent as claimed in claim 1 wherein said first retention means comprises a loop-shaped formation integral with said coiled section.

3. The stent as claimed in claim 2 wherein said loop-shaped formation has a predetermined outer diameter greater than the passage diameter of said ureter where said ureter enters said bladder, to enable said loop-shaped formation to resist movement into said ureter.

4. The stent as claimed in claim 2 wherein said loop-shaped formation lies in an axial plane of the helix of coils of said coiled section.

5. The stent as claimed in claim 1 wherein said second retention means comprises a curl-shaped formation integral with said coiled section.

6. The stent as claimed in claim 5 wherein said curl-shaped formation extends less than 360°.

7. The stent as claimed in claim 5 wherein said curl-shaped formation has a curvature of predetermined magnitude greater than the passage diameter of said ureter where said ureter enters said renal pelvis, to enable said curl-shaped formation to resist movement into said ureter.

8. The stent as claimed in claim 7 wherein said first retention means comprises a loop-shaped formation integral with said coiled section and having an outer diameter of predetermined magnitude greater than the passage diameter of said ureter where said ureter enters said bladder, to enable said loop-shaped formation to resist movement into said ureter, whereby said loop-shaped formation and said curl-shaped formation, upon respective positioning in the bladder and in the renal pelvis, prevent migration of said stent in said ureter.

9. The stent as claimed in claim 5 wherein said curl-shaped formation lies in an axial plane of the helix of coils of said coiled section.

10. The stent as claimed in claim 9 wherein said first retention means comprises a loop-shaped formation integral with said coiled section and said loop shaped formation and said curl shaped formation lie in the same plane.

11. The stent as claimed in claim 1 further including a fluid infusion member joined to said distal end portion for connection to an external fluid source to permit fluid from the fluid source to pass through the infusion tube into said lumen and into said renal pelvis, drainage of said fluid from said pelvis occurring through said ureter as supported by said coiled section.

12. A ureteral infusion and drainage system comprising,
   (a) A stylet, and
   (b) a spiral ureteral stent comprising a relatively flexible, helically shaped, coiled section selectively formable into an approximate straight configuration, said coiled section having a diameter substantially equivalent to that of a normal, unimpaired ureter, to support said ureter, a first retention means for holding said stent in a fixed position in the ureter, at the distal end of said coil section adapted to be received in the bladder, a second retention means for holding said stent in a fixed position in a ureter, at the proximal end of said coiled section adapted to be received in the renal pelvis, and a lumen extending through the entire length of the stent to provide a fluid passage and to permit the use of the stylet to straighten said coiled section and said first and second retention means to facilitate the placement of the stent in the ureter.

13. The system as claimed in claim 12 further including an infusion member joined to the distal end of said stent for connection with an external fluid source to infuse fluid through said stent.

14. The system as claimed in claim 13 wherein said infusion member is detachably secured to said distal end.

15. A ureteral infusion and drainage system comprising,
    (a) a flexible stent having a proximal free end portion and a distal free end portion,
    (b) a lumen in said stent extending from the free end of said proximal end portion to the free end of said distal end portion,
    (c) said stent having a normally coiled section constituted by a plurality of coils in a form of a helix, said proximal and distal end portions extending from opposite portions of said coiled section,
    (d) retaining means for retaining said stent in a ureter respectively formed at said proximal and distal end portions, said retaining means normally having respective curved configurations at said proximal and distal end portions, and
    (e) an elongated straightening member having a predetermined stiffness, insertable in said lumen for straightening the normally curved configurations of said retaining means and for straightening the normally coiled section such that said stent has a relatively straight, substantially uncoiled and uncurved configuration to facilitate insertion of said stent in a ureter, said straightening member being removable from said stent after said stent is positioned in said ureter to permit the coiled section and the curved configuration of the retaining means to reform.

16. The system as claimed in claim 15 wherein said elongated straightening member comprises a wire stylet.

17. The system as claimed in claim 15 wherein the proximal end portion has an opening of reduced size relative to the size of said lumen to prevent projection of said straightening member out of said opening.

18. The system as claimed in claim 15 wherein an infusion member is joined to one of said retaining means for infusing fluid through said stent.

19. A method of infusing and draining the renal pelvis comprising:
    (a) forming a stent of a flexible biocompatible material with curved retaining means at the distal and proximal ends of the stent for respective placement in the bladder and renal cavity to prevent movement of the stent in the ureter,
    (b) including a lumen in the stent extending the full length of the stent,
    (c) forming a flexible helically-shaped coiled section of the stent intermediate the proximal and distal ends of the stent, with a coil diameter substantially the same as that of a normal unimpaired ureter, to support the ureter,
    (d) rendering the stent selectively deformable into an approximately straight configuration by inserting a stylet in the lumen to straighten the coiled section and the retaining means at the proximal and distal ends,
    (e) positioning the straightened stent and stylet assembly within the ureter,
    (f) withdrawing the stylet from the lumen to reform the coiled section and the first and second retaining means, such that the coiled section exerts an outward pressure on any collapsed areas in the ureter to restore the ureter passage to its more normal dimension, and
    (g) permitting drainage of fluid from the renal pelvis through the ureter as supported by the coiled section.

20. The method as claimed in claim 19 including infusing fluid from an external source through the lumen into the renal pelvis.

* * * * *